US00PP14041P39

(12) United States Plant Patent
Carruth

(10) Patent No.: US PP14,041 P3
(45) Date of Patent: Aug. 5, 2003

(54) SHRUB ROSE PLANT NAMED 'WEKAJAZOUL'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 2 days.

(21) Appl. No.: 09/918,155

(22) Filed: Jul. 30, 2001

(65) Prior Publication Data

US 2003/0024017 P1 Jan. 30, 2003

(51) Int. Cl.[7] ..... A01H 5/00

(52) U.S. Cl. ..... Plt./102

(58) Field of Search ..... Plt./102

(56) References Cited

U.S. PATENT DOCUMENTS

PP7,978 P * 9/1992 Twomey ..... Plt./108

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new variety of shrub rose suitable for garden decoration, having flowers of buff white coloration.

1 Drawing Sheet

BOTANICAL CLASSIFICATION

*Rosa hybrida.*

BACKGROUND OF THE INVENTION

This invention relates to a new and distinct variety of Shrub Rose. The varietal denomination of the new variety is 'WEKajazoul'. It has as its seed parent the variety known as 'TWOadvance' (U.S. Plant Pat. No. 7,978) and as its pollen parent an un-disseminated seedling of my creation.

The new variety is a rose plant of the shrub rose class.

SUMMARY OF THE INVENTION

Among the features which distinguish the new variety from other presently available and commercial rose cultivars known to the inventor are the following combination of characteristics: its tall very upright growing habit, its large clusters composed of many single petaled flowers and its petal edges that are moderately reflexed inward. The plant has a very upright growing habit, suitable for outdoor garden decoration.

Asexual reproduction of the new variety by budding as performed in Kern County and Upland, Calif., shows that the foregoing and other distinguishing characteristics come true to form and are established and transmitted through succeeding propagation. 'WEKajazoul' may be asexually propagated by cuttings, budding and grafting.

COMPARISON WITH PARENT

The new rose may be distinguished from its seed parent, 'TWOadvance' by the following combination of characteristics: whereas 'WEKajazoul' bears flowers of buff white coloration, 'TWOadvance' bears flowers of blended orange coloration. The new variety bears very large clusters of medium-sized blooms whereas the seed parent bears significantly smaller clusters with significantly larger flowers.

The new variety may be distinguished from its pollen parent, an un-disseminated seedling of my creation by the following combination of characteristics: whereas 'WEKajazoul' bears medium sized flowers of buff white coloration, the pollen parent bears smaller flowers of yellow coloration. The new variety has a very tall upright growth habit with large leaves, the seed parent has a more spreading to near-climbing growth habit with significantly smaller foliage.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color values are based upon the Colour Chart of The Royal Horticultural Society (1966) except where common terms of color definition are employed.

DESCRIPTION OF THE NEW VARIETY

The following description is of the new variety grown outdoors in Upland, Calif. during the month of May. The characteristics observed below were taken on 3 to 4 years old plants. Phenotypic expression may vary with environmental, cultural and climatic conditions, as well as differences in conditions of light and soil.

FLOWER

The new variety bears its flowers usually in clusters of five or more flowers per stem. Flowers are borne in regular moderately rounded to somewhat flat clusters on strong long stems (about 80 to about 150 cm.). Outdoors, the plant blooms nearly continuously during the growing season. The flowers have a slight tea fragrance.

BUD

The peduncle is about 2.3 to about 4.4 cm. in length, of average caliper (about 0.2 to about 0.3 cm in diameter) and usually erect. It is almost smooth, with some stipitate glands and numerous hairs. Peduncle color is between 138C and 144B sometimes lightly suffused, especially on the side exposed to the sun, with between 185C and 183D.

Before the calyx breaks, the bud is about 0.8 to about 1.4 cm. in diameter at the widest point, about 2.5 to about 3.4 cm. in length, and very pointed in shape with a conspicuous hypanthium. The surface of the bud bears few moderately slender foliaceous appendages and some stipitate glands, usually with slender entire foliaceous parts extending beyond the tip of the bud about ½ or more of its length. Bud color is between 138C and 144B sometimes lightly suffused, especially on the side exposed to the sun, with between 185C and 183D.

The sepals are about 2.7 to about 3.3 cm. in length and about 0.5 to about 0.8 cm. in width at the widest point. The outer surface of the sepal is between 138C and 144B sometimes lightly suffused with between 185C and 183D. The inner surface of the sepal is near 138C. The inner surface of the sepals is covered with fine wooly tomentum; sepal margins are lined with few stipitate glands and hairs.

As the petals open (after the calyx breaks), the bud is about 1.2 to about 1.7 cm. in diameter at the widest point, about 2.7 to about 3.6 cm. in length, and very pointed in form. On the under surface of the newly opened petals, at the point where the petal attaches, there is a moderately large zone between 13C and 12C that gradually suffuses toward the petal edge to between 39C and 29B. On the upper surface of the newly opened petals, at the point where the petal attaches, there is a moderately large zone between 13C and 12C that gradually suffuses toward the petal edge to between 35C and 29C.

BLOOM

When fully open, the bloom ranges from about 5.2 to about 7.5 in diameter. Petalage is single to semi-double with about 5 to 8 petals and about 1 to 3 petaloids arranged irregularly. When partially open, the bloom form is very cupped and the petals are somewhat loosely cupped with petal edges somewhat reflexed inward. When fully open, the bloom and petal form are more loosely cupped with petal edges moderately reflexed inward.

PETALS

The substance of the petals is moderately heavy and somewhat thick, with upper surfaces somewhat satiny and under surfaces are more matte in texture. The outer petals are moderately obovate to somewhat rounded in shape with rounded to somewhat mucronate apices. The inner petals are more obovate to slightly rounded in shape with rounded to somewhat mucronate apices. The petals are about 3.1 to about 3.7 cm. in length and about 2.6 to about 3.8 cm. in width at the widest point. Petal margins are entire.

NEWLY OPENED FLOWER

The under surface of the outer, intermediate and inner petals is between 49C and 38D. At the point where the petal attaches, there is a moderately large zone of between 5D and 12D. The upper surface of the outer, intermediate and inner petals is between 49D and 38D. At the point where the petal attaches, there is a somewhat large zone of between 5C and 12D.

The general tonality of the newly opened flower is between 49D and 38D.

THREE-DAY-OLD FLOWER

The under and upper surface of the outer and inner petals is between 56D and 155C. There is no specific variation between the petal color and the point where the petal attaches.

The general tonality of the three-day-old flower is between 56D and 155C.

On the spent bloom, the petals usually drop off cleanly.

In May in Upland, Calif., blooms on the bush growing outdoors generally last about three to five days. Cut roses from plants grown outdoors and kept at normal indoor living temperatures generally last about three to five days.

MALE REPRODUCTIVE ORGANS

Stamens are many in number (average about 125) and are arranged regularly about the pistils; a few are mixed with petaloids. The filaments are of moderately to long length (about 0.6 to about 0.8 cm.), most with anthers. Filaments are between 7B and 9B. The anthers are moderately large for the class and all open approximately at the same time. Anther color is between 21B and 22B when immature. Anther color at maturity is near 161A. Pollen is abundant.

FEMALE REPRODUCTIVE ORGANS

Pistils vary in number (average about 40). The styles are moderately even, moderately long in length (about 0.4 to about 0.5 cm.), average in caliper and moderately separated to somewhat bunched. Stigma color is near 8A. Style color is near 2D sometimes lightly blushed near the top with near 53C. Ovaries are usually all enclosed in the calyx.

Hips are moderately long in length (about 2.4 to about 2.8 cm.), moderately ovoid to somewhat pear-shaped in form, and near 28A in color when ripe. The hip surface is almost entirely smooth with some hairs and with moderately thick fleshy walls. The sepals are very permanent and usually straight to somewhat recurved in shape. The seeds are irregularly rounded, smooth in texture, approximately 1 to 5 per hip, about 0.2 to about 0.4 cm. in diameter at the widest point and between 165B and 165C in color.

FOLIAGE

The compound leaves are usually comprised of three to five or more leaflets and are borne abundantly. The five-leaflet leaves are about 8.5 to about 12.7 cm. in length and about 7.1 to about 9.8 cm. in width at the widest point, moderately leathery to somewhat crisp in texture and moderately glossy in finish. The terminal leaflets are about 5.2 to about 7.2 cm. in length and about 2.7 to about 4.2 cm. in width at the widest point, shaped ovate to somewhat oval with acute to somewhat acuminate apices and rounded bases. The margins are usually simply serrate.

The upper surface of the mature leaf is between 147A and 136B. The under surface of the mature leaf is between 147B and 138B. The upper surface of the young leaf is between 144A and 138B, sometimes moderately suffused with between 187B and 183B. The under surface of the young leaf is between 138B and 144B, sometimes moderately suffused with between 187C and 183C.

The rachis is average to somewhat heavy in caliper and moderately rough. The upper side is moderately grooved with some hairs and few stipitate glands on the edges of the grooves. The under side of the rachis is moderately rough with very few stipitate glands and a few small prickles. The rachis color is between 147B and 138B.

The stipules are about 1.0 to about 1.8 cm. in length and somewhat wide (about 0.4 to about 0.7 cm.) with moderately straight points that usually turn out at an angle of more than 45 degrees. The stipules color is between 147B and 138B.

The petiole is about 1.4 to about 1.9 cm. in length and about 0.1 to about 0.2 cm in diameter at the widest point. The petiole color is between 147B and 138B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a very upright tall growing habit (about 160 to about 205 cm. in height and about 80 to about 115 cm. spread at the widest point), with very full branching. It displays very vigorous growth.

The color of the major stems is between 138B and 146B. They bear some large prickles that are about 0.7 to about 1.1 cm. in length. The large prickles are almost straight, hooked slightly downward with a medium length somewhat narrow oval base; prickle color is between 165A and 166B. The major stem bears no small prickles.

The color of the branches is between 146A and 138A. They bear some large prickles which are of similar size and shape to the large prickles on the major stems; prickle color is between 165B and 165C. The branches bear very few small prickles of similar shape and coloration.

The color of the new shoots is between 138B and 144B sometimes moderately suffused with between 187B and 183A. They bear some large prickles which are of similar size and shape to the large prickles on the major stems; prickle color is between 187A and 187B. The shoots bear few small prickles of similar shape and coloration.

I claim:

1. A new and distinct shrub rose plant of the variety substantially as described and illustrated herein.

* * * * *

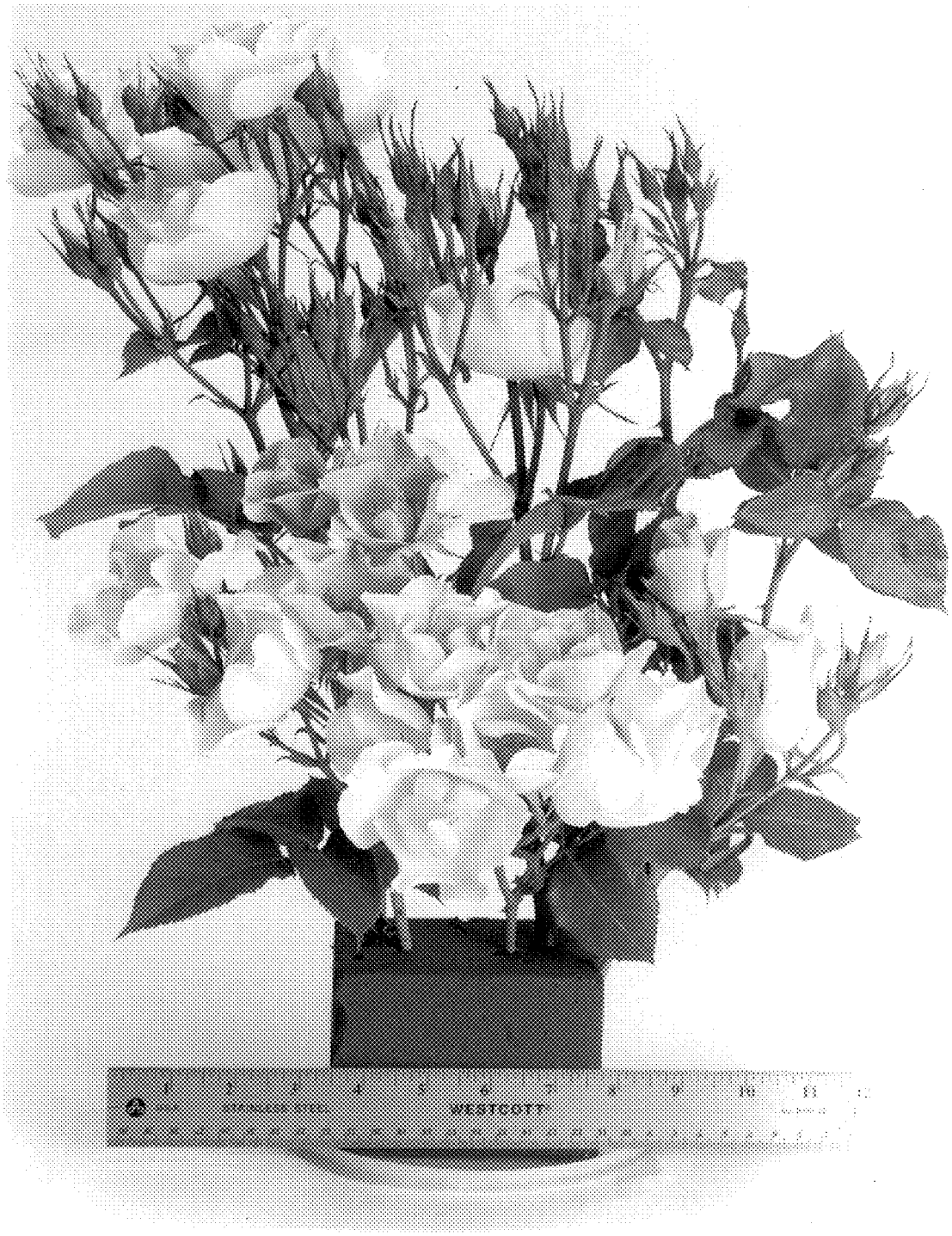
WESTCOTT